United States Patent [19]

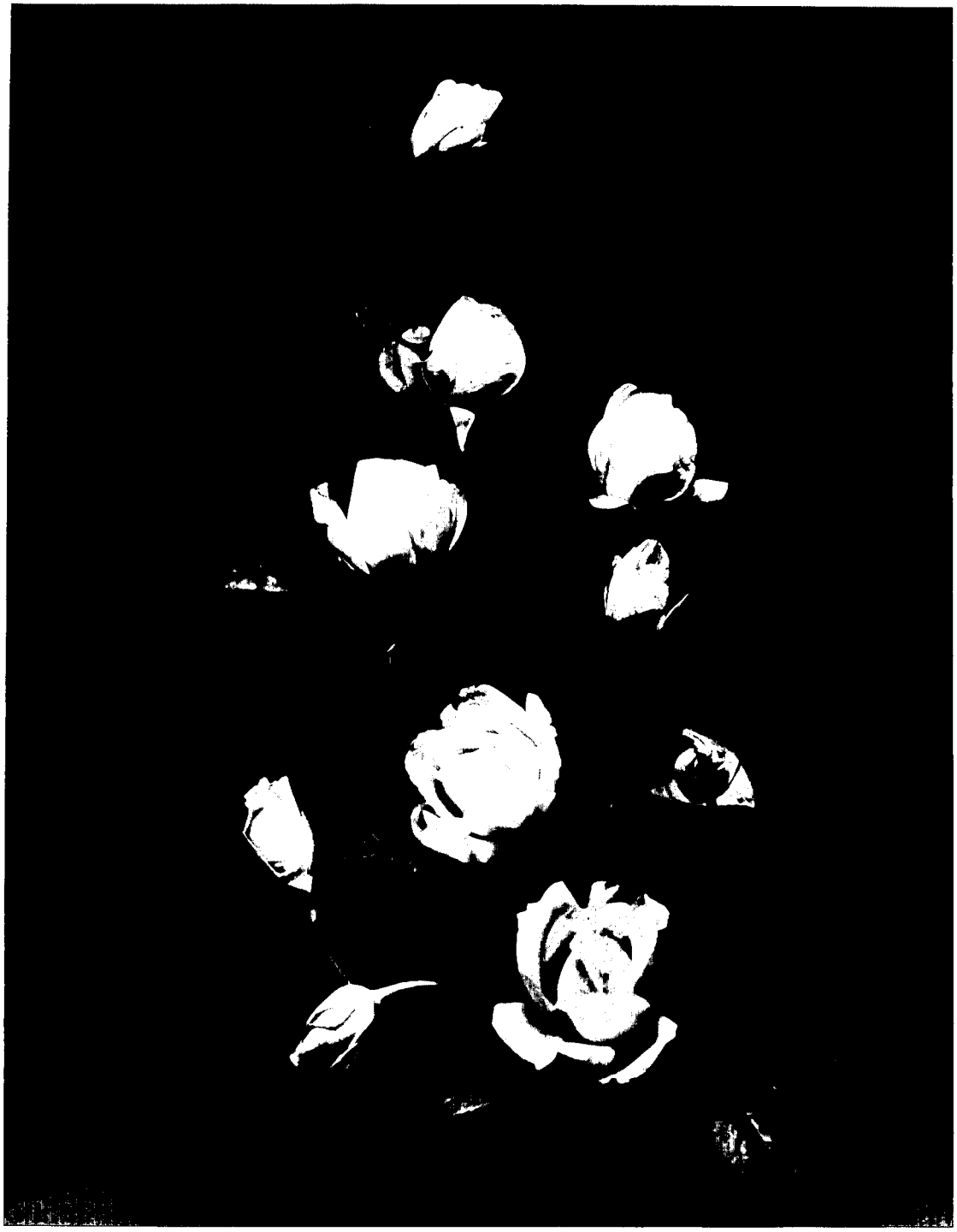

Buck

[11] Patent Number: Plant 5,756

[45] Date of Patent: Jul. 1, 1986

[54] ROSE PLANT NAMED BUCBLU

[75] Inventor: Griffith J. Buck, Ames, Iowa

[73] Assignee: Iowa State University Research Foundation, Inc., Ames, Iowa

[21] Appl. No.: 672,697

[22] Filed: Nov. 19, 1984

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Tilton, Fallon, Lungmus

[57] ABSTRACT

A new variety of hybrid tea rose plant having profuse production of violet-blue flowers of excellent color stability. The plant is also notable for the precociousness with which lateral buds develop and the survivability of the plant under winter conditions without cold weather protection.

1 Drawing Figure

BACKGROUND OF THE NEW PLANT

This new hybrid tea rose cultivar originated as a seedling resulting from a crossing of an unnamed seed parent with an unnamed pollen parent. The seed parent was derived as follows: (Sterling Silver×Intermezzo)×(Sterling Silver×Simone). Sterling Silver is covered by U.S. Plant Pat. No. 1,433, Intermezzo by U.S. Plant Pat. No. 2,430, and Simone by U.S. Plant Pat. No. 1,847. The pollen parent was derived as followed: (Music Maker)×(Mainzer Fastnacht×Tom Brown). The new variety was discovered by me in 1975, at Iowa State University Horticulture Greenhouses, Ames, Iowa, in the course of breeding efforts to produce ever-blooming strains of hybrid tea roses over a wide range of flower colors and a capability of withstanding winter cold. Such breeding efforts began in about 1949 and were carried out by me at the University in Ames, Iowa.

Following its discovery, this new plant has been asexually reproduced under my direction at Ames, Iowa and Tyler, Tex. by cuttings and by bud-grafting. Such propagation through successive generations has shown that the distinctive characteristics of the new variety hold true from generation to generation and appear to be firmly fixed.

DESCRIPTION OF THE DRAWING

This new variety of rose plant is illustrated by the accompanying photographic drawing which has been hand-colored to show one of its blooms in color, the remainder of the photograph being in black and white only.

DESCRIPTION OF THE NEW PLANT

The following is a description, in detail, of this new variety of hybrid tea rose plant with color designations according to The R.H.S. Colour Chart (R.H.S.C.C.) published by The Royal Horticultural Society of London, England, in collaboration with The British Colour Council (B.C.C.), such designations being supplemented in some cases with the descriptive color designations adapted by B.C.C.

THE PLANT

Origin: Seedling.

Parentage:

*Seed parent.*—An unnamed variety resulting from (Sterling Silver×Intermezzo)×Sterling Silver×Simone).

*Pollen parent.*—An unnamed variety obtained by crossing (Music Maker)×(Mainzer Fastnacht×Tom Brown).

Classification:

*Botanic.*—Rosa hybrida.

*Commercial.*—Hybrid Tea Rose.

Form: An erect bush.

Height: About 95 to 110 cm., but taller in areas with a longer growing season.

Growth: Sturdy and vigorous.

Habit: Free branching and erect with strong canes and stems.

Foliage: Abundant.

*Leaves.*—Medium Size. Texture: Smooth and leathery. Color: Upper side — Medium Olive Green 137A (R.H.S.C.C.). Under side — Medium Olive Green 137C (R.H.S.C.C.) with a faint reddish tinge in the young stage. Leaflets: 5 to 7 in number, and of obovate to round-obovate shape.

Petioles: About 2 to 3 cm. in length.

Rachis: Prickly, about 4.0 to 6.5 cm. in length.

Thorns and prickles: The plant lacks thorns, spines, and corms, but has prickles that are about 3 to 5 mm. in length and have a coloration of Red-Purple 74C (R.H.S.C.C.).

THE BUD

Size: Medium large, having a diameter of about 2.5 to 3.0 cm. and a depth of about 4 cm.

Form: Ovoid and pointed.

Opening: The buds open slowly.

Color: When the sepals first divide, the buds are light Hyacinth Blue 91B (R.H.S.C.C.). That color is retained when the petals begin to unfurl, but with a tinting of Champagne 164D (R.H.S.C.C.) at the base.

Sepals: The sepals are spear-shaped and tend to curl back.

*Color.*—Inside — Light Olive Green 138B (R.H.S.C.C.). Outside — Medium Olive Green 138B (R.H.S.C.C.).

Calyx:

*Shape.*—Funnel-shaped.

*Size.*—Small, about 1 cm. in width and 1 cm. in length.

*Aspect.*—Smooth.

*Splitting.*—Calyx does not split.

Peduncle:

*Length.*—About 5 to 6 cm. long.

*Aspect.*—Smooth and erect.

*Strength.*—Strong and erect.

*Color.*—Medium Olive Green 138B (R.H.S.C.C.).

THE FLOWER

Blooming habit: Profuse and continuous from early to late in the season.

Size: Large, having a diameter of about 11.0 to 12.5 cm. and a depth of about 4 to 6 cm.

Borne: Singly and in clusters.

Shape: Cup-shaped when the bloom first opens, becoming a more shallow cup shape when the flower develops.

Petalage:

*Number of petals.*—35 to 45 including petaloids.

*Arrangement.*—Imbricated.

*Form.*—Broadly cordate.

*Color.*—The outer and inner petals are Lobelia Blue 91C (R.H.S.C.C.) on both sides.

Petaloids:

*Number.*—1 to 6.

*Size.*—About 2 cm. long and about 1 cm. wide.

*Color.*—Lobelia Blue 91C (R.H.S.C.C.).

Peduncle:

*Length.*—5 to 6 cm.

*Color.*—Mid Olive Green 138B (R.H.S.C.C.).

*Character.*—Sturdy and upright.

Persistence: The flowers shatter with age.

Disease resistance: Moderately tolerant of Blackspot and Powdery Mildew.

Fragrance: Sweetly fragrant.

Lasting quality: About 4 to 5 days on the plant; 5 to 6 days as a cut flower.

REPRODUCTIVE ORGANS

Stamens:

*Anthers.*—Numerous (75 to 100) with a length of about 2 to 3 cm. and in a circular arrangement.

*Filaments.*—The filaments have a length of about 15 to 18 mm. with a color of Dresden Yellow 5B (R.H.S.C.C.).

*Pollen.*—The color of the pollen is yellow.

*Pistils.*—Numerous, with a length of about 1.0 to 1.4 cm.

*Stigmas.*—Color is reddish.

*Ovaries.*—Ovoid, with hispid achenes attached to the receptacle wall.

FRUIT

The fruit is moderately fertile and ovoid in shape with a yellow-orange color at maturity.

This new variety resembles Soir d' Automne, but with flowers darker in color. A distinguishing characteristic of this variety is not only in the light violet-blue color of its profuse and continuously blooming flowers, but in the stability of that color over the life of each flower. Older flowers have essentially the same coloration as the younger flowers, resulting in a more uniform and stable coloration of the blooms in comparison with other cultivars of the hybrid tea class of roses. Also, this variety differs in the precociousness with which the lateral buds begin growth after the terminal flower bud appears. Resistance to winter temperature conditions, as may be experienced in Midwestern United States (Iowa), is also a notable characteristic of this new variety.

I claim:

1. A new and distinct variety of rose plant substantially as herein shown and described, characterized by its profuse production of large flowers of violet-blue color, its precocious development of lateral buds, its ability to survive without protection under adverse winter conditions, and the stability of the coloration of its blooms.

* * * * *